US009401135B2

(12) United States Patent
Davis et al.

(10) Patent No.: US 9,401,135 B2
(45) Date of Patent: Jul. 26, 2016

(54) TRANSDUCER WITH DRY ADHESIVE COUPLANT

(71) Applicant: The Boeing Company, Chicago, IL (US)

(72) Inventors: Keith J. Davis, Seattle, WA (US); Richard H. Bossi, Renton, WA (US); John A. Mittleider, Kent, WA (US); Arthur M. Vetter, Renton, WA (US)

(73) Assignee: THE BOEING COMPANY, Chicago, IL (US)

( * ) Notice: Subject to any disclaimer, the term of this patent is extended or adjusted under 35 U.S.C. 154(b) by 298 days.

(21) Appl. No.: 14/011,216

(22) Filed: Aug. 27, 2013

(65) Prior Publication Data

US 2015/0059479 A1   Mar. 5, 2015

(51) Int. Cl.
*G01N 29/22* (2006.01)
*G10K 11/02* (2006.01)
*G01N 29/28* (2006.01)

(52) U.S. Cl.
CPC ............... *G10K 11/02* (2013.01); *G01N 29/28* (2013.01); *G01N 2291/0422* (2013.01)

(58) Field of Classification Search
CPC ... G01N 29/28; G01N 29/22; G01N 29/2412; G01K 11/02
USPC .................................................. 73/644, 643
See application file for complete search history.

(56) References Cited

U.S. PATENT DOCUMENTS

| 3,732,444 | A | * | 5/1973 | Miller | 73/644 |
| 4,582,077 | A | * | 4/1986 | Gabriel et al. | 134/94.1 |
| 2001/0029782 | A1 | * | 10/2001 | Articolo | 73/314 |
| 2008/0011060 | A1 | * | 1/2008 | Lynnworth | 73/64.53 |
| 2009/0011232 | A1 | * | 1/2009 | Dai et al. | 428/355 R |
| 2012/0032380 | A1 | * | 2/2012 | Riachentsev | 269/8 |
| 2012/0234073 | A1 | * | 9/2012 | Knorr | 73/1.13 |
| 2014/0217643 | A1 | * | 8/2014 | Nikawa et al. | 264/299 |

OTHER PUBLICATIONS

Acker, F., "New Adhesives Based on Gecko Foot Geometry Offer Substantial Benefits in a Huge Variety of Applications," Ingenia, Issue 30, pp. 39-42 (Mar. 2007).
Yurdumakan, B. et al., "Synthetic gecko foot-hairs from multiwalled carbon nanotubes," Chem. Commun., 2005, pp. 3799-3801.
Qu, L. et al., "Carbon Nanotube Arrays with Strong Shear Binding-On and Easy Normal Lifting-Off," Science, vol. 322, pp. 238-242 (Oct. 2008).
"Supporting Online Material Carbon Nanotube Arrays with Strong Shear Binding-On and Easy Normal Lifting-Off," (Qu, L. et al.), Science, vol. 322, 238 (2008), www.sciencemag.org/cgi/content/full/322/5899/238/DC1.
Komsky, I.N., "Polymer substrates for dry-coupled ultrasonic transducers," Proc. of SPIE, vol. 5047, pp. 74-83 (2003).
Hu, S. et al., "Strong Adhesion and Friction Coupling in Hierarchical Carbon Nanotube Arrays for Dry Adhesive Applications," ACS Applied Materials & Interfaces, 4, pp. 1972-1980 (2012).
"Supplementary Information for Strong Adhesion and Friction Coupling in Hierarchical Carbon Nanotube Arrays for Dry Adhesive Applications," (Hu, S. et al.), ACS Applied Materials & Interfaces, 4, pp. 1972-1980 (2012).
Hu, S., "Gecko and Bio-Inspired Hierarchical Fibrillar Adhesive Structures Explored by Multiscale Modeling and Simulation" (Aug. 2012).

* cited by examiner

*Primary Examiner* — Helen Kwok
(74) *Attorney, Agent, or Firm* — Thompson Hine LLP

(57) ABSTRACT

A transducer for stimulating an article under test with ultrasonic vibration may include a transducer body having a transmitting face and configured to generate ultrasonic vibration through the transmitting face, and an couplant mounted on the transmitting face, the couplant having a multiplicity of vertically aligned carbon nanotubes extending therefrom in a direction substantially normal to the transmitting face.

16 Claims, 6 Drawing Sheets

TRANSDUCER WITH DRY ADHESIVE COUPLANT

FIELD

The disclosure relates to transducers and, more particularly, a transducer having a couplant between the transducer and the article under test.

BACKGROUND

Nondestructive evaluation of materials and bonds frequently requires the transmission of ultrasound waves into the material or bond to be evaluated. Ultrasound waves may be transmitted into the material by placing a transducer, which generates ultrasound waves, on a surface of the article under test. One form of ultrasound testing involves transmitting ultrasound shear waves into the material under test, with the wave propagation direction perpendicular to the surface of the material under test. The shear waves generated by a shear wave transducer may provide greater spatial resolution than the more commonly used longitudinal waves at a given frequency, and can provide other complementary data.

Acoustic impedance mismatch between ambient air and the solids, such as the material of the article under test, may be large. In such circumstances, nearly all of the energy generated by the transducer in the form of ultrasound shear waves may be reflected and very little transmitted into the article under test. In order to counteract this effect, a couplant is employed to displace the air between the transducer and the surface of the article under test, thereby making it possible to transmit more sound energy into the test specimen so that a useable ultrasonic signal can be obtained.

In contact ultrasonic testing where the face of a transducer body through which sound waves are transmitted is placed against a corresponding surface of the material under test, the couplant may take the form of a thin film of oil, glycerin or water that is placed between the face of the transducer body and the surface of the material under test. Other types of couplants may include the use of a rigid adhesive such as an epoxy, or a highly viscous "honey" couplant.

Such couplants may possess disadvantages. For example, use of an epoxy couplant may result in damage either to the face of the transducer or the article under test upon removal of the transducer from the article under test. Further, use of couplants that are highly viscous, or use of couplants such as glycerin, oil, or water, may be messy and may contaminate the surface of the article under test.

The lack of a feasible couplant for use with ultrasound shear wave transducers has discouraged the use of ultrasound shear wave transducers in spite of the benefits of using ultrasound shear waves to evaluate an article under test. Accordingly, there is a need for a suitable couplant for use with an ultrasound shear wave transducer, as well as other types of transducers.

SUMMARY

In one embodiment, a transducer for stimulating an article under test with ultrasonic vibration may include a transducer body having a transmitting face and configured to generate ultrasonic vibration through the transmitting face, and a couplant mounted on the transmitting face, the couplant having a multiplicity of vertically aligned carbon nanotubes extending therefrom in a direction substantially normal to the transmitting face.

In another embodiment, a transducer for stimulating an article under test with ultrasonic vibration may include a transducer body having a transmitting face and configured to generate ultrasonic vibration through the transmitting face, a couplant mounted on the transmitting face, the couplant having a multiplicity of vertically aligned carbon nanotubes extending therefrom in a direction substantially normal to the transmitting face, and a transducer mount configured to hold the transducer body and exert a force on the transducer body sufficient to urge the vertically aligned carbon nanotubes against a surface of an article under test and bend the vertically aligned nanotubes to form an adhesive bond between the couplant and the surface of an article under test.

In yet another embodiment, a method for attaching a transducer to a surface of an article under test may include providing a transmitting face of a transducer body with a couplant, the couplant having a multiplicity of vertically aligned carbon nanotubes extending therefrom in a direction substantially normal to the transmitting face, and applying a force to the transducer body sufficient to urge the vertically aligned carbon nanotubes against the surface of the article under test and bend the vertically aligned nanotubes to form an adhesive bond between the couplant and the surface of the article under test.

Other objects and advantages of the disclosed transducer with dry adhesive couplant will be apparent from the following description, the accompanying drawings, and the appended claims.

DETAILED DESCRIPTION

Figure 1:
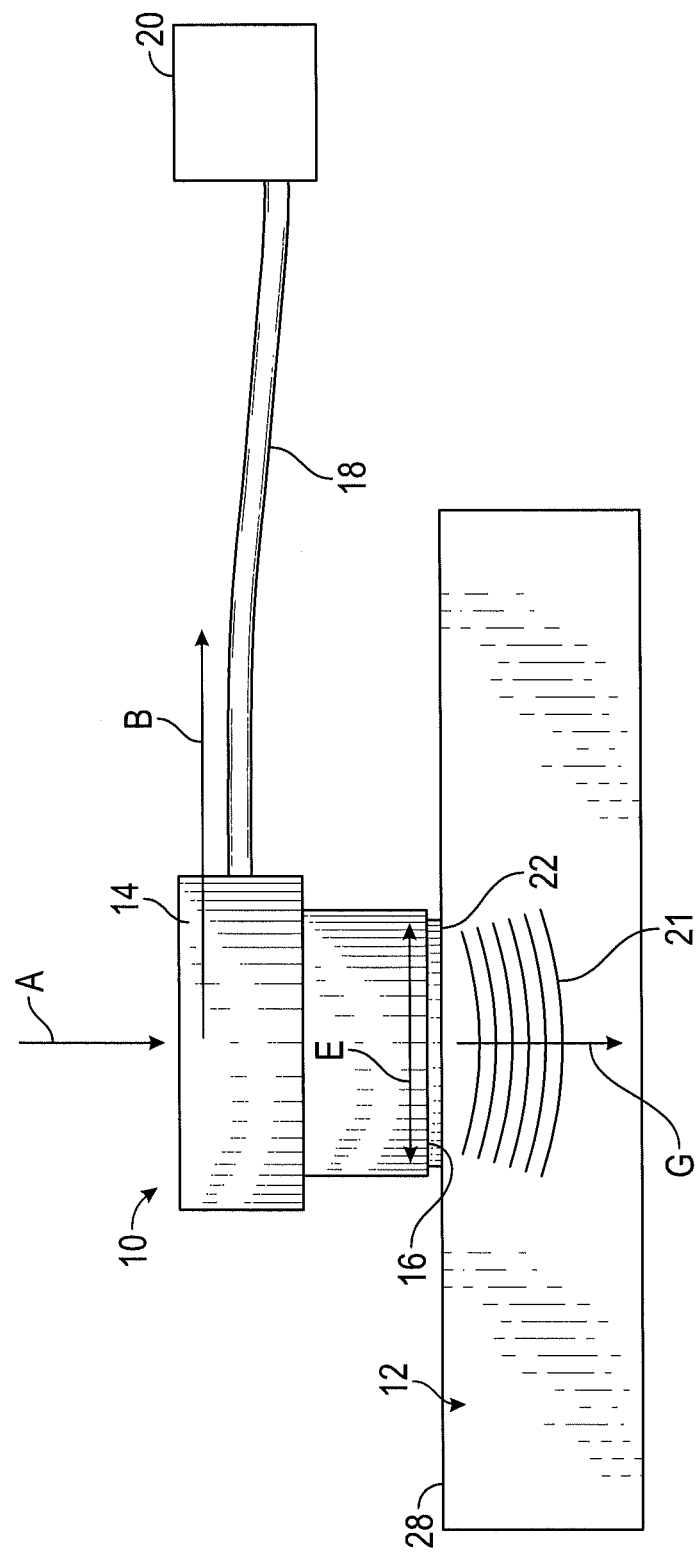
FIG. 1 is a schematic side elevation of an embodiment of the transducer with dry adhesive couplant.

As shown in FIG. 1, the transducer with dry adhesive couplant, generally designated 10, may be used for stimulating an article under test, generally designated 12, with ultrasonic vibration. The transducer 10 may include a transducer body 14 having a transmitting face 16 and which receives electrical power through a cable 18 from a source 20 of electrical power. The transducer 10 may be any transducer capable of converting electrical energy from the source 20 into another form of energy, such as ultrasonic vibration, and transmitting the ultrasonic vibration through the transmitting face 16. In a particular embodiment, the transducer 10 may be a transducer for generating shear wave ultrasound, indicated at 21, through the transmitting face 16. In such an embodiment, the transducer body 14 may oscillate in the direction of arrow E.

Figure 2:
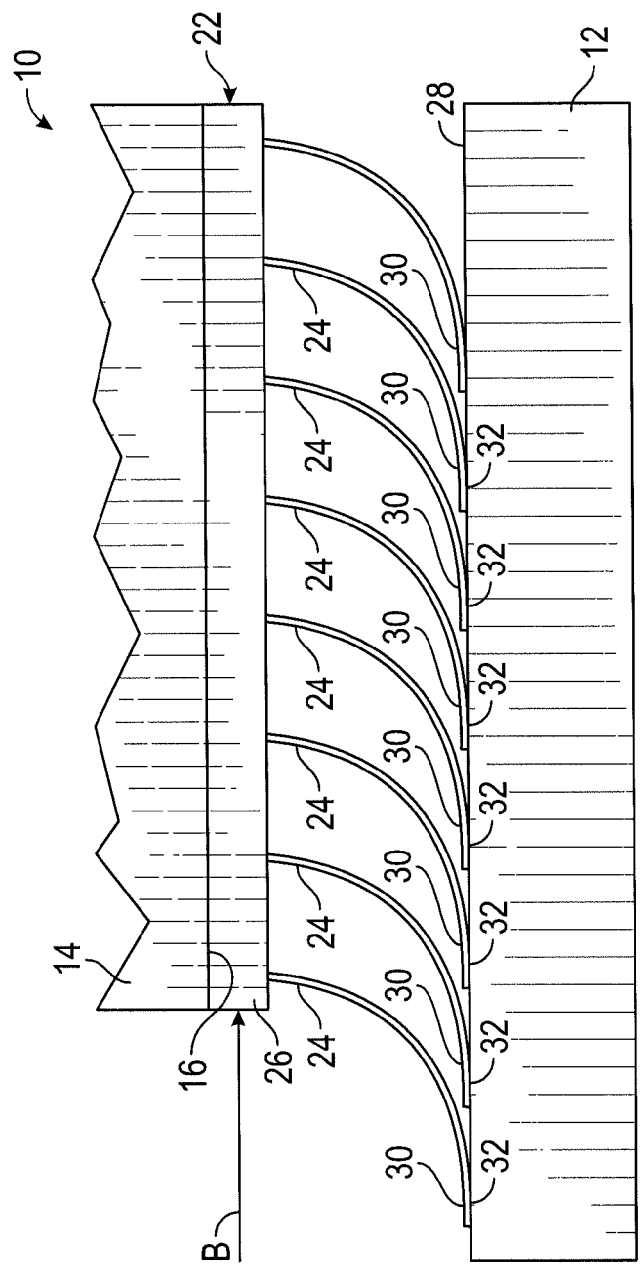
FIG. 2 is a detail of the dry adhesive couplant of the transducer of FIG. 1.

The transducer 10 may include a couplant, generally designated 22, that may be mounted on the transmitting face 16. As shown in FIG. 2, the couplant 22 may include a multiplicity of vertically aligned carbon nanotubes 24 extending therefrom in a direction substantially normal to the transmitting face 16. In an embodiment, the couplant 22 may include a substrate 26 made of a silicon dioxide/silicon. The carbon nanotubes 24 may be attached to the substrate 26 by chemical vapor deposition. In embodiments, the carbon nanotubes 24 may be single-walled nanotubes, multi-walled nanotubes, or a combination of single-walled and multi-walled nanotubes. Such nanotubes 24 may be described in Yurdmakan et al, *Chem. Commun.*, p. 3799 (2005); L. Qu et al., *Science* 322, p. 238 (2008); F. Acker, *Ingenia* 30, p. 42 (2007); S. Hu et al., *ACS Appl. Mater. Interfaces* 4, p. 1972 (2012); and I. Komsky, *SPIE* 5047, p. 74 (2003); the entire contents of all of the foregoing incorporated herein by reference.

In an embodiment, the vertically aligned carbon nanotubes 24 may be present in a density sufficient to form an adhesive bond between the transducer body 14 and a surface 28 of the article under test 12 upon application of a force, indicated by arrow A in FIG. 1 and arrow B in FIGS. 1 and 2, to the body 14 to urge the body and the vertically aligned carbon nanotubes against the surface and to displace the body relative to the surface, once the vertically aligned carbon nanotubes have contacted the surface.

In an embodiment, the vertically aligned carbon nanotubes 24 may be present in a density of between about $10^8$ to $10^{12}$ vertically aligned carbon nanotubes per centimeter squared. As a result, the couplant 22 may form an adhesive bond between the transducer face 16 and the surface 28, which in an embodiment may be a dry adhesive bond. In an embodiment, the vertically aligned carbon nanotubes 24 may be approximately 1 to 500 microns in length.

As shown in FIG. 2, in an embodiment, the force indicated by arrows A and B may be sufficient to urge the transducer body 14 to urge the body and the vertically aligned carbon nanotubes 24 against the surface 28, and to displace the body relative to the surface, sufficiently to bend the vertically aligned carbon nanotubes 24 to allow the tips 30 of the carbon nanotubes to lie flat against the surface 28. In an embodiment, the tips 30 of the vertically aligned carbon nanotubes 24 may provide a surface contact, indicated at 32, with the surface 28 sufficiently large to allow van der Waal's forces to provide substantial adhesion of the tips to the surface and transfer of shear force, indicated by arrow B, between the body 14 and surface 28 of the article under test 12. Thus, the couplant 22 may form a coupling with the surface 28 of the article under test 12.

In another embodiment, if only the normal force indicated by arrow A is exerted on the transducer body 14, the body would be urged only vertically against the surface 28, and the vertically aligned carbon nanotubes 24 would be bent randomly, so that the tips 30 would make good contact with the surface 28, but would not be aligned with each other.

Figure 3A:
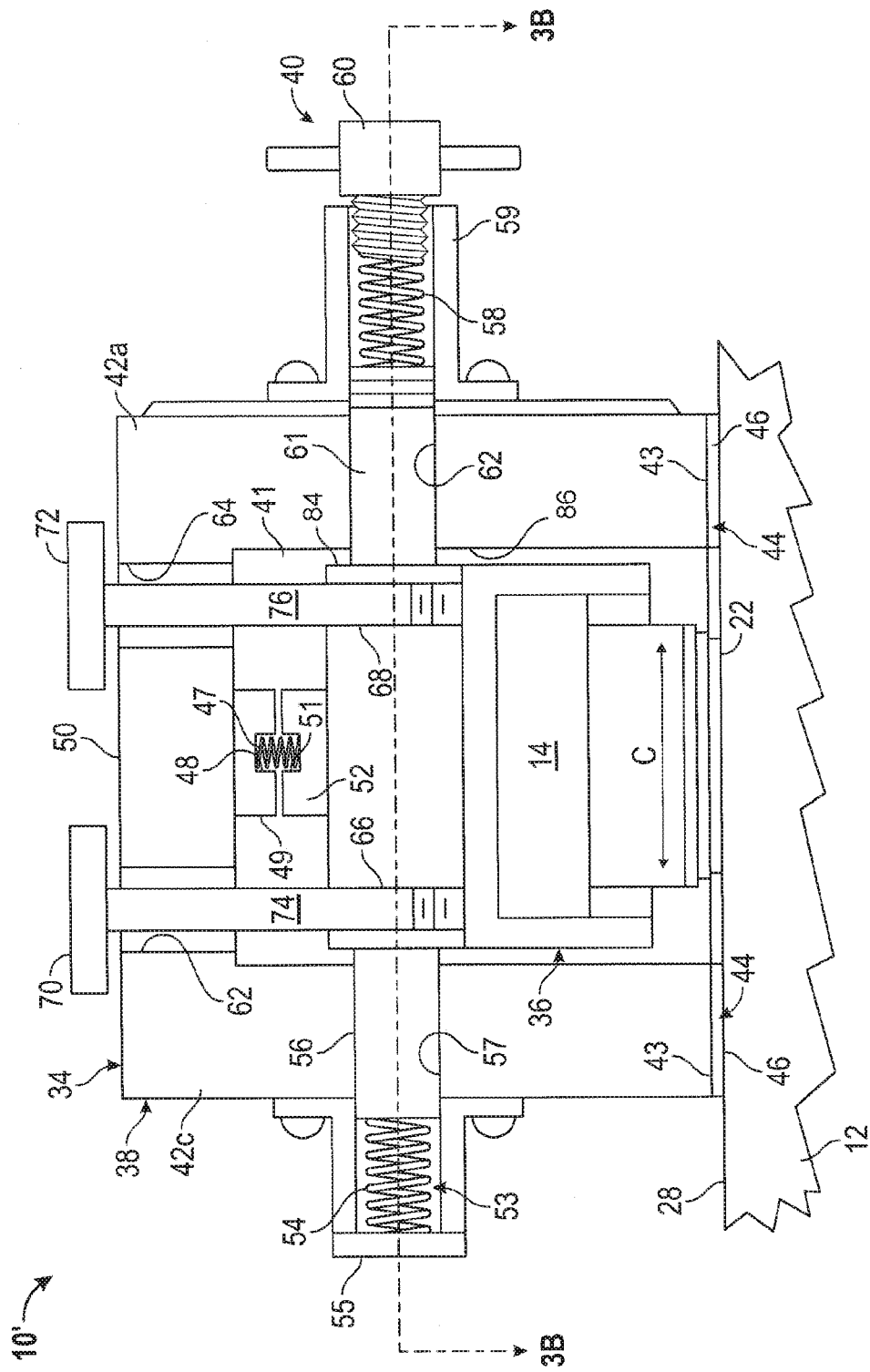
FIG. 3A is a schematic side elevation of another embodiment of the disclosed transducer with dry adhesive couplant, taken at line 3A-3A of FIG. 3b.
Figure 3B:
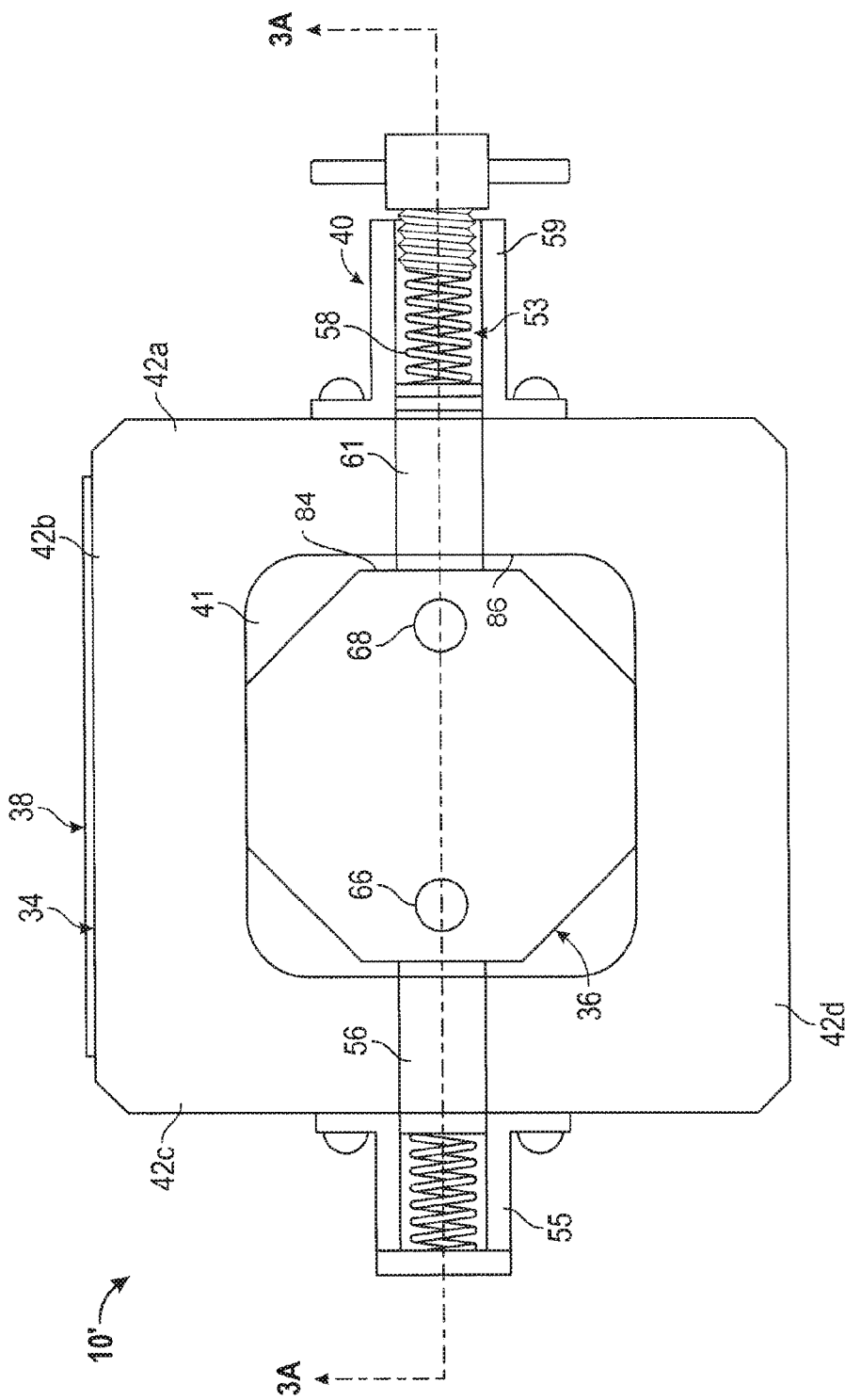
FIG. 3B is a top plan view of the embodiment of FIG. 3A, taken at line 3B-3B of FIG. 3A.

As shown in FIGS. 3A and 3B, an embodiment 10' of the transducer with dry adhesive couplant may include a transducer mount, generally designated 34. In an embodiment, the transducer mount 34 may be configured to hold the transducer body 14 and exert a force on the transducer body sufficient to urge the vertically aligned carbon nanotubes 24 (FIG. 2) against the surface 28 of an article under test 12 and bend the vertically aligned carbon nanotubes to form an adhesive bond between the couplant 22 and the surface of the article under test.

The transducer mount 34 may include a translation stage, generally designated 36, configured to hold the transducer body 14, and a frame 38 configured to support the translation stage 36 above the surface 28 of the article under test 12 for translatable movement relative thereto, and a shear adjuster, generally designated 40, for translating the translation stage 36 and transducer body relative to the frame and the surface of the article under test 12.

In an embodiment, the frame 38 may include an inner volume 41 shaped to receive and enclose the translation stage 36 and transducer body 14, and is defined in part by side walls 42a, 42b, 42c, and 42d. The walls 42a-d terminate in a generally rectangular base surface 43 configured to be removably attached to the surface 28 of the article under test 12. The base surface 43 may include pads 44 that may include a removable attachment component, generally designated 46. In embodiments, the removable attachment component 46 may be selected from one or more of a magnet, an adhesive, and a second couplant, the second couplant having a multiplicity of vertically aligned carbon nanotubes extending therefrom in a direction substantially normal to the transmitting surface 16. In embodiments, the removable attachment component 46 may be selected and/or shaped to provide an adhesive force greater than the adhesive force of the couplant 22 of the transducer body 14.

In embodiments, the transducer 10' may include a normal resilient element, which in the embodiment shown may take the form of at least one compression spring 47, configured to exert a force against the translation stage 36 to urge the transducer body 14 against the surface 28. An upper portion of the compression spring 47 may be received within the recess 48 in an upper spring mount 49 attached to a top wall 50 of the frame 38. A lower portion of the spring 47 may be received in a recess 51 in a lower spring mount 52 of the translation stage.

The shear adjuster 40 may include a shear resilient element, generally designated 53, which in the embodiment shown may include a light spring 54 captured within housing 55 that may be attached to wall 42c of the mount 34. Light spring 54 may be seated within housing 55 and may urge against a plunger 56 that passes through an opening 57 in wall 42c and, in turn, urges against the translation stage 36. The shear adjuster 40 also may include a relatively stiff spring 58, having a spring constant greater than that of the light spring 54, that may be positioned within a housing 59 attached to wall 42a opposite the light spring.

The relatively stiff spring 58 may be attached at an outer end to an adjustment screw 60 that threadedly engages the housing 59, and may be attached at an inner end to a plunger 61 that passes through an opening 62 in wall 42a of the frame 38 to contact the translation stage 36. The stiff spring 58 may be seated on and urged by the adjustment screw 60 to urge the plunger 61 against the translation stage 36.

Thus, the shear resilient element 53 may include a light spring 54 extending from the frame 38 toward the translation stage 36, a first plunger 56 extending between the light spring and the translation stage, a stiff spring 58, having a spring constant greater than a spring constant of the light spring, extending from the frame toward the translation stage in an opposite direction, and a second plunger 61 in between the stiff spring and the translation stage. The shear resilient element 53 may be employed to position the translation stage 36 laterally (i.e., in the direction of arrow C) within the inner volume 41 relative to the frame 38 and surface 28. In embodiments, both plungers 56, 61 urge against the translation stage 36, but may not be rigidly fixed to the translation stage, and so may allow vertical movement of the translation stage relative to the plungers and the frame 38.

The top wall 50 of the frame 38 may include openings 62, 64 that receive cap screws 66, 68, respectively that may thread into the translation stage 36. In other embodiments, the screws 66, 68 may be pressed into holes formed in the translation stage 36, brazed or welded to the translation stage, joined by adhesives, or by other suitable means of attachment. the screws 66, 68 include heads 70, 72 shaped to be larger than the openings 62, 64, and shanks 74, 76 sized to be smaller than the openings 62, 64 to allow translation of the translation stage 36 within the inner volume.

The shanks 74, 76 each have a length such that the heads 70, 72 are spaced from the top wall 50 when the couplant 22 is adhered to the surface 28 of the article under test 12. When the mount 34 is not attached to an article under test 12, the screws 66, 68 may allow the translation stage 36 to slide downwardly relative to the frame 38, and slide relative to plungers 56, 61, so that at least the couplant 22 protrudes below the attachment component 46 of the frame. Thus, when the frame is attached to the surface 28, the compression spring 47 may be compressed, thereby urging the translation stage 36, transducer body 14 and couplant 22 against the surface.

In operation, the transducer 10, 10' may be attached first to the surface 28 of the article under test 12. As shown in FIG. 1, a vertical or normal force in the direction of arrow A may be applied to the transducer body 14, either by a device such as a cylinder motor or by hand (not shown). This vertical force may be applied initially, or may be a sustained force applied to the transducer body 14 throughout the test. In either case, the normal force may be sufficient to compress the vertically aligned nanotubes 24 against the surface 28.

A shear force in the direction of arrow B may then be applied to slightly displace the transducer body 14 and couplant 22 relative to the surface 28 of the article under test 12. This displacement may act to bend the tips 30 of the nanotubes 24 to form a contact surface 32 with the surface 28 of the article under test 12. When the nanotubes 24 are first formed on the substrate 22, the tips 30 typically may be tangled with each other. By pressing the transducer body 14 downwardly and in the direction of arrow A and sidewardly in the direction of arrow B, some or all of the tips 30 may become aligned with each other, as shown in FIG. 2.

In an embodiment in which the transducer 10, 10' is a shear wave transducer, the applied shear force in the direction of the arrow B may be in substantially the same direction as the direction of oscillation of the shear waves 21 produced by the transducer, as shown by arrow E in FIG. 1. In other embodiments, the shear force applied to a transducer 10, 10' in the form of a shear wave transducer in the direction of applied shear force indicated by arrow B may be skewed relative to the direction of oscillation of the shear waves indicated by arrow E in FIG. 1, provided that the vector component of applied shear force in the direction of arrow E may be greater than the amplitude of the oscillation indicated by arrow F in FIG. 4. In still other embodiments, the direction of applied shear force indicated by arrow B may be such that there is little or no vector component in the direction of oscillation indicated by arrow E.

Figure 5:
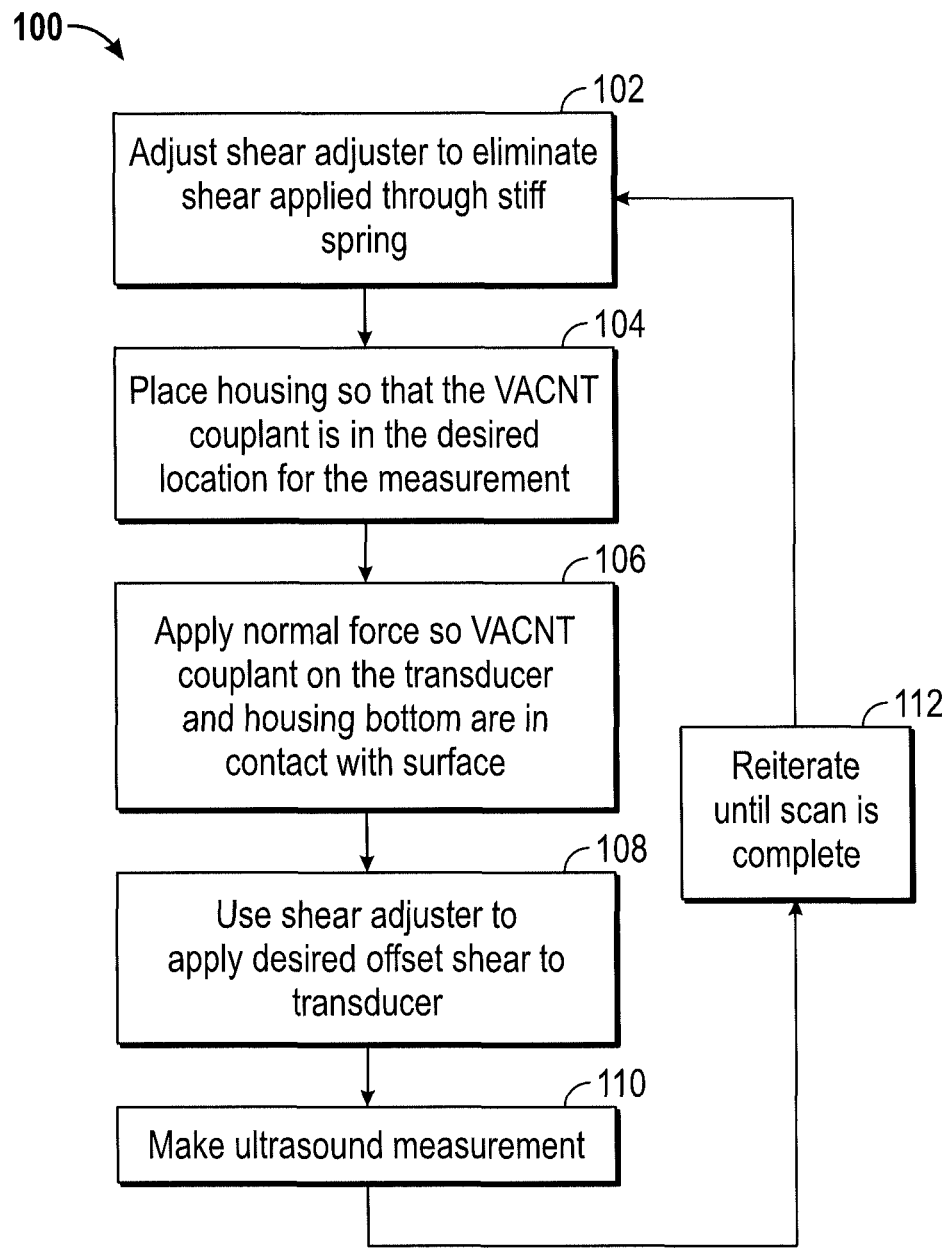
FIG. 5 is a flow chart showing a method of using the transducer disclosed in FIGS. 3A and 3B.

With respect to the embodiment of the transducer 10' in FIGS. 3A and 3B, a process for use is shown in the flowchart 100 of FIG. 5. Initially, as indicated in block 102, the shear adjuster 40 may be adjusted to eliminate shear applied through the stiff spring 58. Thumb screw 60 may be backed out of the housing 59 sufficiently to allow a side surface 84 of the translation stage 36 to be urged against and contact an inner surface 86 of wall 42a by light spring 54, thus eliminating the shear force applied by the relatively stiff spring 58.

As indicated in block 104, the housing 34 may be positioned so that the vertically aligned carbon nanotubes (VACNT) 24 are in the desired location on the surface 28 for measurement. The frame 38 then may be placed on the surface 28 of the article under test 12 and the removable attachment component 44 fixes the frame to the surface in the desired location for measurement. In an embodiment, the translation stage 36 may be positioned within the frame 38 such that the couplant 22 extends downwardly slightly below the frame so that the couplant contacts the surface 28 of the article under test 12 before the frame does, when the frame is placed upon the surface.

As indicated in block 106, a normal force may be applied so that the vertically aligned carbon nanotubes 24 on the transducer 10' and bottom of the housing 34 are in contact with the surface 28. The normal resilient element in the form of spring 47 may urge the translation stage 36 downwardly to apply a normal or vertical force in the direction of arrow A in FIG. 1 on the transducer body 14. This force may place the couplant 22 in contact with the surface 28, and in particular, may place the vertically aligned carbon nanotubes 24 in contact with the surface.

As indicated in block 108, the shear adjuster 40 then may be used to apply the desired offset shear to the transducer 10'. Thumb screw 62 of the shear adjuster 40 then may be turned to actuate the shear adjuster 40 to apply a desired offset shear to the transducer body 14 and nanotubes 24. In FIG. 3A, this may take the form of a movement of the translation stage 36 and transducer body 14 to the left in the direction of arrow C. This may result in the side surface 84 becoming separated from the inner surface 86. In embodiments, this movement may be approximately the same as a length of the carbon nanotubes 24. In embodiments, this may be approximately 1-500 microns.

As indicated in block 110, at this time an ultrasound measurement may be made by the transducer 10' on the article under test 12. As indicated in block 112, the process of blocks 102-110 may be reiterated at other locations on surface 28 until the scan is complete.

Figure 4:
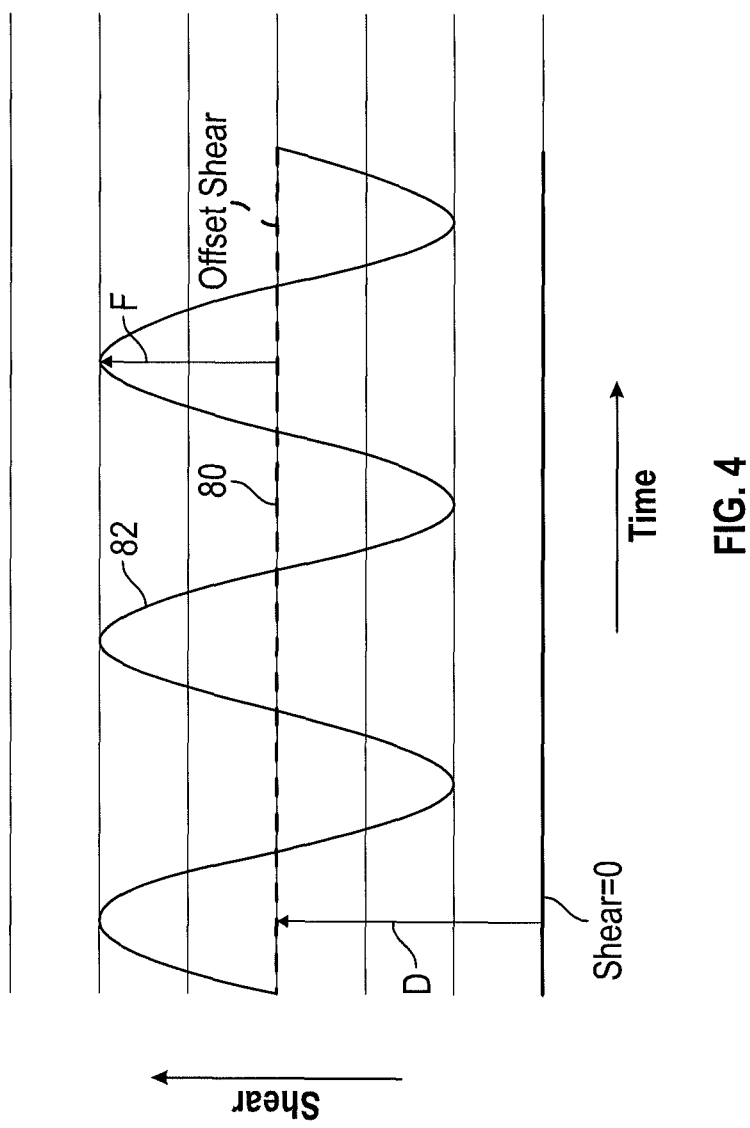
FIG. 4 is a graph of shear versus time of the transducers disclosed in FIGS. 1-3.

As shown in FIG. 4, with the embodiments of FIGS. 1 and 2, and FIGS. 3A and 3B, the transducer body 14 and couplant 22 preferably may form a coupling with the surface 28 by applying a force to the transducer body to urge the body and the vertically aligned carbon nanotubes 24 against the surface, and to displace the body relative to the surface, once the vertically aligned carbon nanotubes have contacted the surface, a distance represented by line 80 that is a distance D that is greater than the amplitude, represented by arrow F, of the shear wave ultrasonic vibrations transmitted by the transducer body 14, which in an embodiment may be shear waves resulting from oscillations in the direction of arrow E in FIG. 1. This displacement may ensure that a sufficient amount of shear, resulting in the tips 30 of the nanotubes 24 making contact at 32 with the surface 28, will be present as the transducer body 14 oscillates in the direction of arrow C (FIG. 3A), as indicated by the sine wave 82. This amount of displacement may be necessary to prevent the inadvertent separation or weakening of the connection formed by the vertically aligned carbon nanotubes 24 of the couplant 22 during a test.

The transducer body 14 may generate shear waves 21 (FIG. 1) that travel or propagate in the direction of arrow G, namely, in a direction substantially normal to the transmitting face 16 of the transducer body and substantially normal to the surface 28 of the article under test 12. After the test has been completed, the transducer 14 may be lifted vertically away from the surface 28 of the article under test 12. The attachment and removal of the couplant 22 (and mount 34 if a similar couplant is used to attach the frame 36 to the surface 28) to and from the surface may not mark or otherwise contaminate the article under test 12. In an embodiment, the adhesive force provided by van der Waal's forces between the tips 30 of the vertically aligned carbon nanotubes 24 and the surface 28 of the article under test 12 may provide a shear strength of up to 90 N/cm². The force required for detachment of the transducer 10, 10' is roughly an order of magnitude lower than that observed in shear.

While the forms of apparatus and methods disclosed may constitute preferred embodiments of the disclosed transducer with dry adhesive couplant, it is to be understood that variations may be made therein without departing from the scope of this disclosure.

What is claimed is:

1. A shear wave transducer for stimulating an article under test with ultrasonic vibration, the transducer comprising:
    a transducer body having a transmitting face and configured to generate ultrasonic vibration through the transmitting face;
    a couplant mounted on the transmitting face, the couplant having a multiplicity of vertically aligned carbon nanotubes extending therefrom in a direction substantially normal to the transmitting face; and
    a coupling formed by the couplant with a surface of an article under test, wherein the coupling is formed by applying a force to the body to urge the body and the vertically aligned carbon nanotubes against the surface, and to displace the body relative to the surface, once the vertically aligned carbon nanotubes have contacted the surface, a distance greater than an amplitude of a shear wave transmitted by the shear wave transducer.

2. The transducer of claim 1, wherein the couplant includes a silicon dioxide/silicon substrate with vertically aligned carbon nanotubes attached thereto by chemical vapor deposition.

3. The transducer of claim 1, wherein the vertically aligned carbon nanotubes are present in a density sufficient to form an adhesive bond between the body and a surface of the article under test upon application of a force to the body to urge the body and the vertically aligned carbon nanotubes against the surface and to displace the body relative to the surface, once the vertically aligned carbon nanotubes have contacted the surface.

4. The transducer of claim 3, wherein the vertically aligned carbon nanotubes are present in a density of between about $10^8$ to $10^{12}$ vertically aligned carbon nanotubes per centimeter squared.

5. The transducer of claim 4, wherein the adhesive bond is a dry adhesive bond.

6. The transducer of claim 1, wherein the vertically aligned carbon nanotubes are approximately 1 to 500 microns in length.

7. The transducer of claim 1, wherein the coupling is formed by applying a force to the body to urge the body and the vertically aligned carbon nanotubes against the surface, and to displace the body relative to the surface, sufficiently to bend the vertically aligned carbon nanotubes to allow tips of the vertically aligned carbon nanotubes to lie flat against the surface.

8. The transducer of claim 7, wherein the tips of the vertically aligned carbon nanotubes provide a surface contact with the surface sufficiently large so that van der Waal's forces provide substantial adhesion of the tips to the surface and transfer of shear forces between the body and the surface.

9. The transducer of claim 1, further comprising a transducer mount, the transducer mount having a translation stage configured to hold the transducer body; a frame configured to support the translation stage above a surface of an article under test for translatable movement relative thereto; and a shear adjuster for translating the translation stage and transducer relative to the frame and the surface.

10. The transducer of claim 9, wherein the frame includes pads configured to be removably attached to the surface.

11. The transducer of claim 10, wherein the pads include a removable attachment component selected from one or more of a magnet, an adhesive, and a second couplant, the second couplant having a multiplicity of vertically aligned carbon nanotubes extending therefrom in a direction substantially normal to the transmitting surface.

12. The transducer of claim 9, wherein the frame includes a normal resilient element configured to exert a force against the translation stage to urge the transducer body against a surface; and the shear adjuster includes a shear resilient element and an adjustment screw for displacing the translation stage and transducer body relative to the frame.

13. The transducer of claim 12, wherein the shear resilient element includes a light spring extending from the frame toward the translation stage; a first plunger extending between the light spring and the translation stage; a stiff spring having a spring constant greater than a spring constant of the light spring, extending from the frame toward the translation stage in an opposite direction; and a second plunger in between the stiff spring and the translation stage.

14. A shear wave transducer for stimulating an article under test with ultrasonic vibration, the transducer comprising:
    a transducer body having a transmitting face and configured to generate ultrasonic vibration through the transmitting face;
    a couplant mounted on the transmitting face, the couplant having a multiplicity of vertically aligned carbon nanotubes extending therefrom in a direction substantially normal to the transmitting face;
    a coupling formed by the couplant with a surface of an article under test; and
    a transducer mount configured to hold the transducer body and exert a force on the transducer body sufficient to urge the vertically aligned carbon nanotubes against a surface of an article under test and bend the vertically aligned nanotubes to form an adhesive bond between the couplant and the surface of an article under test, wherein the coupling is formed by the transducer mount applying a force to the body to urge the body and the vertically aligned carbon nanotubes against the surface, and to displace the body relative to the surface, once the vertically aligned carbon nanotubes have contacted the surface, a distance greater than an amplitude of a shear wave transmitted by the shear wave transducer.

15. A method for attaching a shear wave transducer to a surface of an article under test, the method comprising:
    providing a transmitting face of a transducer body with a couplant, the couplant having a multiplicity of vertically aligned carbon nanotubes extending therefrom in a direction substantially normal to the transmitting face; and
    applying a force to the transducer body sufficient to urge the vertically aligned carbon nanotubes against the surface of the article under test and bend the vertically aligned nanotubes to form an adhesive bond between the couplant and the surface of the article under test, and sufficient to displace the tips of the vertically aligned carbon nanotubes relative to the surface, once the vertically aligned carbon nanotubes have contacted the surface, a distance greater than an amplitude of a shear wave transmitted by the shear wave transducer in a direction substantially the same direction as an oscillation direction of the shear wave transducer.

16. The method of claim 15, wherein applying a force includes applying a shear force sufficient to displace the vertically aligned carbon nanotubes parallel to the surface of the article under test.

\* \* \* \* \*